United States Patent
Bai et al.

(10) Patent No.: US 10,830,743 B2
(45) Date of Patent: Nov. 10, 2020

(54) DETERMINING THE NET EMISSIONS OF AIR POLLUTANTS

(71) Applicant: International Business Machines Corporation, Armonk, NY (US)

(72) Inventors: Long Sheng Bai, Xiamen (CN); Liang Liu, Beijing (CN); Zhuo Liu, Beijing (CN); Jun Mei Qu, Beijing (CN); Wei Zhuang, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 616 days.

(21) Appl. No.: 15/586,523

(22) Filed: May 4, 2017

(65) Prior Publication Data
US 2018/0321208 A1 Nov. 8, 2018

(51) Int. Cl.
*G01N 33/00* (2006.01)
*G01W 1/02* (2006.01)
*G06N 20/00* (2019.01)
*G06N 3/08* (2006.01)

(52) U.S. Cl.
CPC ......... *G01N 33/0034* (2013.01); *G01W 1/02* (2013.01); *G06N 20/00* (2019.01); *G06N 3/08* (2013.01); *Y02A 50/20* (2018.01)

(58) Field of Classification Search
None
See application file for complete search history.

(56) References Cited

U.S. PATENT DOCUMENTS

| 5,740,463 | A | * | 4/1998 | Oshima | G06F 15/803 |
| | | | | | 712/11 |
| 8,478,566 | B2 | | 7/2013 | Glenn et al. | |
| 8,510,059 | B2 | | 8/2013 | Prince | |
| 2012/0140231 | A1 | * | 6/2012 | Knox | H01L 29/872 |
| | | | | | 356/442 |

(Continued)

FOREIGN PATENT DOCUMENTS

| CN | 102628852 | 12/2014 |
| EP | 2797041 | 10/2014 |
| WO | 2015175304 | 11/2015 |

OTHER PUBLICATIONS

Boubrima et al. "Optimal Deployment of Wireless Sensor Networks for Air Pollution Monitoring", Aug. 3-6, 2015, 24th International Conference on Computer Communication and Networks (ICCCN) (Year: 2015).*

(Continued)

*Primary Examiner* — Alexander Satanovsky
*Assistant Examiner* — Brent A. Fairbanks
(74) *Attorney, Agent, or Firm* — Fleit Intellectual Property Law; Jon Gibbons

(57) ABSTRACT

A method for determining a source of pollutant emissions for a selected area includes: mapping a grid onto a representation of the selected area; collecting monitoring data for the selected data; from the monitoring data, assigning air pollution values and weather values to each cell in the grid using an interpolation method to estimate values for gap cells; re-sizing the grid to mitigate the influence of atmospheric turbulence on the air pollution values; and using weather factor separation to minimize the influence of weather from the air pollution values, resulting in air pollution values that reflect the net pollutant emissions for the selected area.

21 Claims, 16 Drawing Sheets

(56) References Cited

U.S. PATENT DOCUMENTS

| | | | |
|---|---|---|---|
| 2013/0035870 A1 | 2/2013 | Feng et al. | |
| 2013/0110400 A1* | 5/2013 | Moshe | G01N 1/26 702/3 |
| 2014/0257782 A1* | 9/2014 | Davis | G06F 30/20 703/9 |
| 2015/0006712 A1* | 1/2015 | Khann | H04L 67/22 709/224 |
| 2015/0339811 A1* | 11/2015 | Zhong | G06T 7/0002 382/104 |
| 2017/0227509 A1* | 8/2017 | Chang | G01N 33/007 |

OTHER PUBLICATIONS

Swaminathan, N., "Module 5R18: Environmental Fluid Mechanics and Air Pollution", University of Cambridge, Department of Engineering, Sep. 2014, http://www.eng.cam.ac.uk/uploads/pages/files/5r18syllabus-general.pdf, p. 1.

Baklanov, A., "Application of CFD methods for modelling in air pollution problems: possibilities and gaps", Environmental Monitoring and Assessment, Nov. 2000, pp. 181-189, vol. 65, Issue 1.

Karim, A., et al., Modelling reacting localized air pollution using Computational Fluid Dynamics (CFD), Atmospheric Environment, Feb. 2011, pp. 889-895, vol. 45, No. 4.

* cited by examiner $$\Delta t \times S(i,j) = C_{i,j,k+1}(1+f(c,v,h)) - C_{i,j,k} + \alpha(C_{i+1,j,k+1} - C_{i-1,j,k+1}) + \beta(C_{i,j+1,k+1} - C_{i,j-1,k+1})$$

$$\alpha = \frac{\Delta t \cdot u_x}{2\Delta x}, \quad \beta = \frac{\Delta t \cdot u_y}{2\Delta y}$$

$\Delta t$ = TIME INTERVAL OF AIR MONITOR
$u_x, u_y$ = WIND SPEED IN $x,y$ DIRECTION
$\Delta x, \Delta y$ = SIZE OF UNIT GRID

DETERMINING THE NET EMISSIONS OF AIR POLLUTANTS

BACKGROUND

The present disclosure generally relates to air quality reporting, and more particularly relates to evaluating air pollution using weather factor separation and grid analysis.

Indisputably, air pollution has a negative impact on the environment, adversely affecting humans, crops, and animals. Studies have shown that high levels of air pollutants are detrimental to human health, exacerbating health problems such as respiratory ailments and allergies. To counter these deleterious effects, governments across the world have put forth a multi-pronged effort to combat air pollution. For example, federal and local governments in many countries now have legislation to set emission standards and enforce compliance with the emission standards. In addition, governmental incentives such as the electric vehicle tax credit encourage consumers to switch to "cleaner" vehicles.

Today we know that air pollution is diligently monitored, with sensors providing an Air Quality Index (AQI) in real-time. However, pollution studies are complicated by the many different pollutant sources. Monitoring the air quality of a target area provides a measure of the current emission levels for that area; however the monitored air pollutant value can only describe the emission concentration state in real time; it cannot pinpoint the particular source of the pollution because the air quality value is complicatedly related to an initial local concentration state, the pollution source, and weather factors affecting the emissions. In order to control air pollution, we need to pinpoint the local source of the pollution, i.e., the "net emission."

SUMMARY

Briefly, according to an embodiment of the present invention, a method for determining a source of pollutant emissions for a selected area includes: mapping a grid onto a representation of the selected area; collecting monitoring data for the selected data; from the monitoring data, assigning air pollution values and weather values to each cell in the grid using an interpolation method to estimate values for gap cells; re-sizing the grid to mitigate the influence of atmospheric turbulence on the air pollution values; and using weather factor separation to minimize the influence of weather from the air pollution values, resulting in air pollution values that reflect the net pollutant emissions for the selected area.

According to another embodiment of the present invention, an information processing system is configured to determine a location source of pollutant emissions for a selected area. The information processing system includes: a processor device, a memory operably coupled with the processor device, and a database storing monitoring data. The memory stores computer-executable instructions causing a computer to perform: mapping a grid onto a representation of the selected area; collecting monitoring data for the selected data; from the monitoring data, assigning air pollution values and weather values to each cell in the grid using an interpolation method to estimate values for gap cells; re-sizing the grid to mitigate the influence of atmospheric turbulence on the air pollution values; and using weather factor separation to minimize the influence of weather from the air pollution values, resulting in air pollution values that reflect the net pollutant emissions for the selected area.

According to another embodiment of the present invention, a computer program product for determining a location source of pollutant emissions for a selected area includes a non-transitory computer readable storage medium readable by a processing device and storing instructions for execution by the processing device. The instructions include: mapping a grid onto a representation of the selected area; collecting monitoring data for the selected data; from the monitoring data, assigning air pollution values and weather values to each cell in the grid using an interpolation method to estimate values for gap cells; re-sizing the grid to mitigate the influence of atmospheric turbulence on the air pollution values; and using weather factor separation to minimize the influence of weather from the air pollution values, resulting in air pollution values that reflect the net pollutant emissions for the selected area.

BRIEF DESCRIPTION OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

Non-Limiting Definitions

The terms "a", "an" and "the" are intended to include the plural forms as well, unless the context clearly indicates otherwise.

The term "air pollutant" means a substance in the air that affects air quality.

The terms "comprises" and/or "comprising," when used in this specification, specify the presence of stated features, steps, operations, elements, and/or components, but do not preclude the presence or addition of one or more other features, integers, steps, operations, elements, components, and/or groups thereof.

The term "diffusion" means the process of molecules spreading from an area of high concentration to an area of low concentration.

The term "dispersion" means distribution over a wide area.

The term "emission intensity" means the average emission rate of a pollutant from a source, usually expressed as a ratio of emission relative to an activity. For example, we follow the ratio of greenhouse gas emissions produced to the GDP (gross domestic product) of a nation.

The term "emission standards" means legal requirements on pollutant limits.

The term "ETL" refers to "extract, transform, and load"—three functions performed by one tool for moving data from one database to another database.

The term "fluid dynamics" means the study of fluids (liquids and gases) and what affects them.

The term "greenhouse gases" means atmospheric gases that absorb and emit radiation within the thermal infrared range. The primary greenhouse gases are carbon dioxide, water vapor, nitrous oxide, methane, and ozone.

The term "greenhouse effect" means the warming effect of the gases trapped in the atmosphere, similar to the warming effect of a greenhouse.

Figure 1:
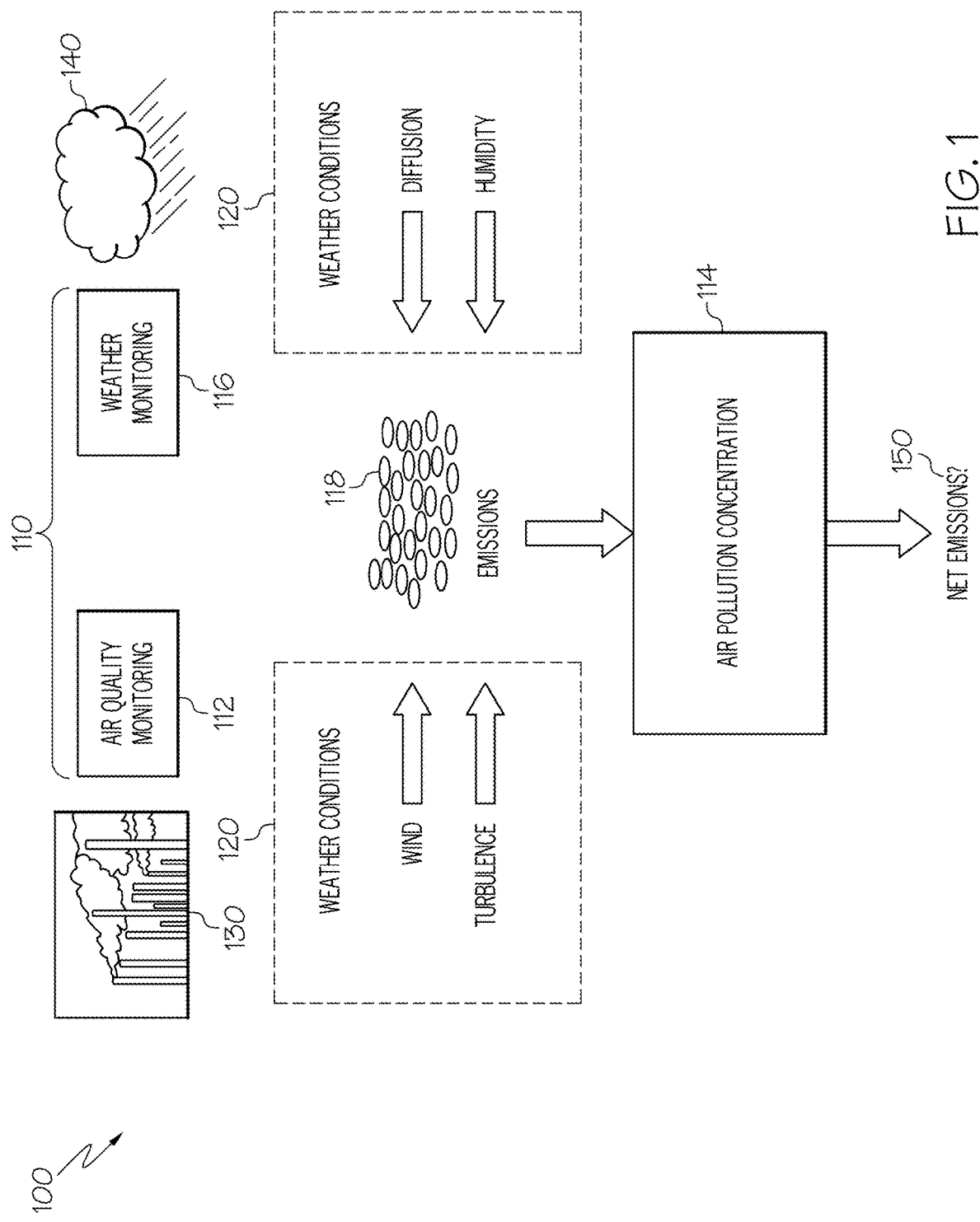
FIG. 1 is a simplified diagram of air quality monitoring.

FIG. 1—Air Quality Monitoring

Referring now to the drawings in general and to FIG. 1 in particular, there is shown a simplified diagram illustrating aspects of present-day air quality monitoring 100. As an example, in China the Ministry of Environmental Protection (MEP) is responsible for air quality monitoring and control. Since 2013 the MEP reports air quality values such as the Air Pollution Index (API) provided by various air quality monitoring sites 112. Air quality monitoring sites 112 are located throughout cities and provinces, with the majority of air quality monitoring sites 112 in urban areas. The air quality monitoring sites 112 have sensors which measure the air pollution 130 in the atmosphere close to ground level, providing an air pollution concentration value 114.

The air pollution concentration value 114 is composed of emissions 118 from gaseous pollutants such as greenhouse gases. In China, the API records levels of six pollutants found in ambient air: nitrogen dioxide ($NO_2$), sulfur dioxide ($SO_2$), carbon monoxide (CO), ozone ($O_3$), $PM_{10}$, and $PM_{2.5}$. $PM_{10}$, and $PM_{2.5}$ are known as breathable particulate matter (PM). These particles are inhalable, measuring up to 10 μm and 2.5 μm in aerodynamic diameter, respectively. Most countries monitor these same six pollutants in determining local air quality.

The problem arises because emissions 118 are heavily influenced by weather conditions 120. Due to the influence of weather conditions 120, the air pollution concentration value 114 reports a combination of emissions 118, both local emissions and emissions from outside sources. Multiple elements contribute to the air pollution concentration value 114. These elements are: wind, diffusion, dispersion, rain, humidity, and the actual pollution source. For example, wind dilutes and disperses air pollution 130 in a horizontal direction, while humidity increases the concentration of pollutant particles in the ambient air, essentially "trapping" the emissions 118 in place. Precipitation also affects the movement and concentration of pollutants in the atmosphere.

In addition, atmospheric turbulence is a random motion that can disperse air pollution 130 in both a horizontal and vertical direction. Turbulence is similar to a whirlpool in a river, where velocity and pressure are unpredictable. This is one of the reasons why a reading of the air pollution concentration value 114 in one area, as measured by an air quality monitoring site 112, can fail to identify the actual location source of the emissions 118.

The weather monitoring sites 116 measure wind speed and wind direction, along with humidity. Atmospheric diffusion is another weather condition 120 that affects the air quality readings. Atmospheric diffusion refers to the movement of pollutants in the atmosphere, while atmospheric dispersion is the spreading out (transport) of emission particles over a large area, reducing their concentration. Dispersion by wind is a main influencing factor, while diffusion is a secondary factor. Diffusion cannot be monitored per se; however we can approximate a diffusion source by locating the source center of a region reporting a high level of air pollution 130.

In order to adequately monitor and control air pollution 130, we need to know the net emissions 150 so that we can reliably source the emissions 118. The sensor readings from a limited amount of air quality monitoring sites 112 can only describe the concentration state, but cannot estimate the net emissions 150 of a studied area because of the influence of various weather conditions 120. Using calculations based on properties of fluid dynamics has limitations because fluid dynamics fails to account for weather conditions 120.

Figure 2:
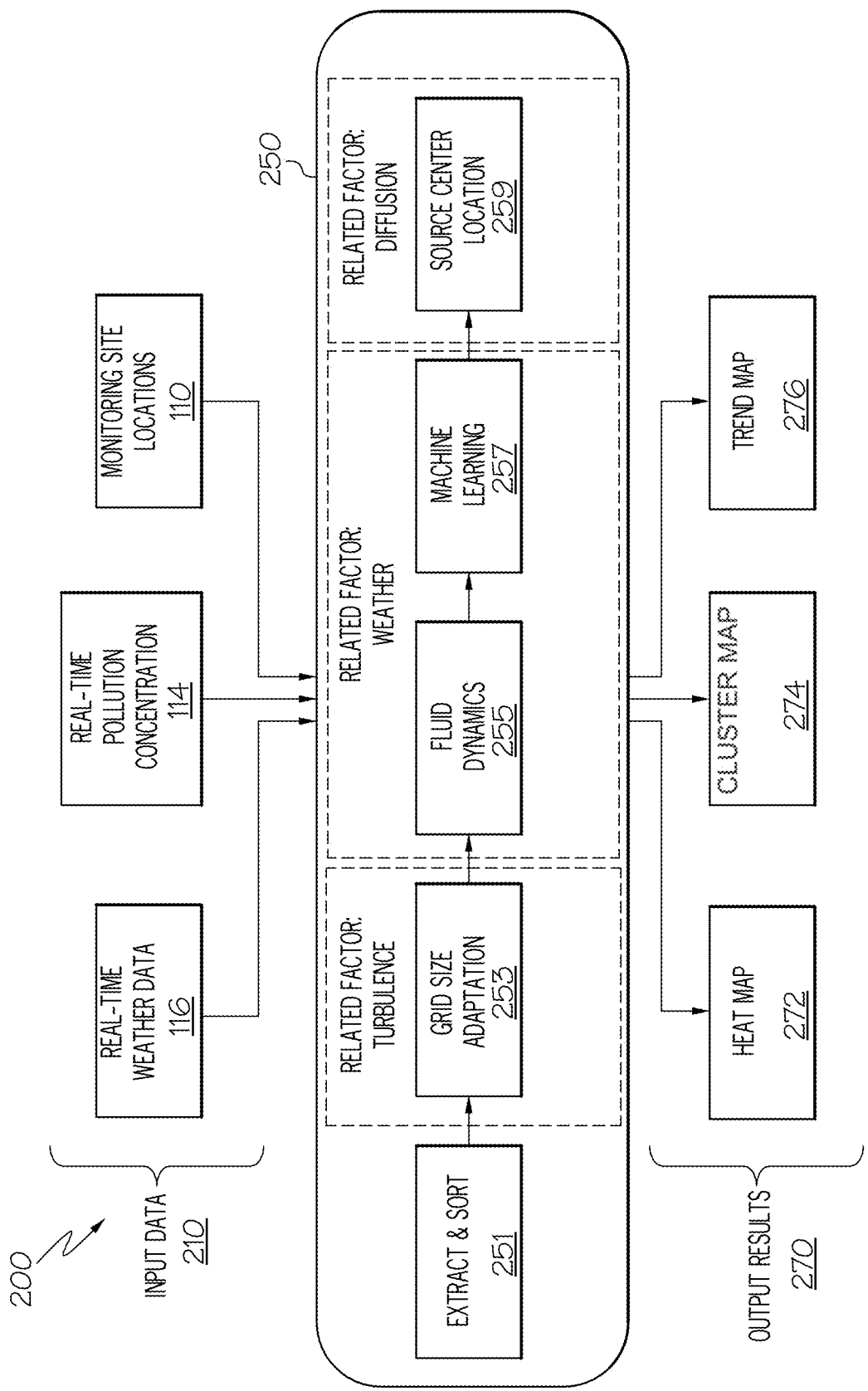
FIG. 2 is a simplified block diagram of a net emissions identification system, according to an embodiment of the present invention.

FIG. 2—Net Emissions Identification System

FIG. 2 shows a simplified block diagram of a system 200 for determining the source of local air pollution 130 based on weather factor separation and grid analysis, according to one embodiment of the invention. The system 200 includes a Net Emissions Identifier 250 that receives input data 210 and produces output data 270 identifying the local sources of air pollution 130, i.e., the net emissions 150. The output data 270 can be provided in a graphical display such as, for example, a heat map 272, a cluster map 274 and a trend map 276.

The inputs to the Net Emissions Identifier 250 are data consisting of: 1) real-time weather data 140 from weather monitoring sites 116 collected over a period of time; 2) a real-time measured air pollution concentration value 114 from air quality monitoring sites 112 collected over a period of time; and 3) the identifiers and locations for the different air quality monitoring sites 112 and weather monitoring sites 116.

The Net Emissions Identifier 250 is an information processor that performs processes represented here by program modules, according to an embodiment of the present disclosure. One with knowledge in the art will appreciate that the Net Emissions Identifier 250 can be a stand-alone device or group of devices. The program modules such as the modules shown in FIG. 2 may include routines, formulas, programs, scripts, objects, components, logic, data structures, algorithms, and so on that perform particular tasks or implement particular abstract data types. The Net Emissions Identifier 250 is configured to perform the entire process for determining a source of net emissions 150 automatically, with the output from one module/process/step becoming the input to the next module/process/step. Some of the processes are performed off-line and some processes are performed in real-time.

The modules are depicted in FIG. 2 as separate hardware components; however the modules can be embodied as hardware, software, or a combination of hardware and software. The tasks performed by the modules can be distributed across devices. The information processing system 200 may be practiced in various computing environments such as conventional and distributed computing environments where tasks are performed by remote processing devices that are linked through a communications network. In a distributed cloud computing environment, program modules may be located in both local and remote computer system storage media including memory storage devices.

The program modules are:

1) Extract and Sort Module 251. This module extracts and sorts the local air pollution 130 data from the air quality monitoring sites 112 and the weather data 140 from the weather monitoring sites 116. A tool such as Extract, Transform, and Load (ETL) can be utilized to perform the data extraction and sorting. The raw data is tagged with an identifier of the monitoring site from which it was collected.

2) Grid Size Adaptation Module 253. This module determines an optimal size of a grid in order to minimize the influence of atmospheric turbulence. In one embodiment, determining the optimal grid size means determining the cell-size of the grid cells in a two-dimensional grid, which also determines how many cells make up the grid. For example, assume a grid with n=100 cells has a cell size which maps to 200 square meters on a city map. Re-sizing the cells in the grid to increase their size to correlate to 400 square meters reduces the number of cells to n=50. Therefore, for purposes of this discussion, increasing the grid size means increasing the size of the grid cells; likewise, decreasing the grid size means decreasing the size of the grid cells.

3) Fluid Dynamics Calculation Module 255. For each grid cell, this module minimizes the weather influence from the adjacent cells in the grid by building a relationship among the local emissions source, the air pollution concentration value 114, and wind value.

4) Machine Learning and Feedback Module 257. For each grid cell, this module uses data from a background value area as the training and testing dataset to build a machine learning model used to mitigate the influence of weather conditions 120 in the cell.

5) Source Center Location Module 259. This module finds the source center of a region of a high level of air pollution 130 using, for example, a cluster method.

Figure 3:
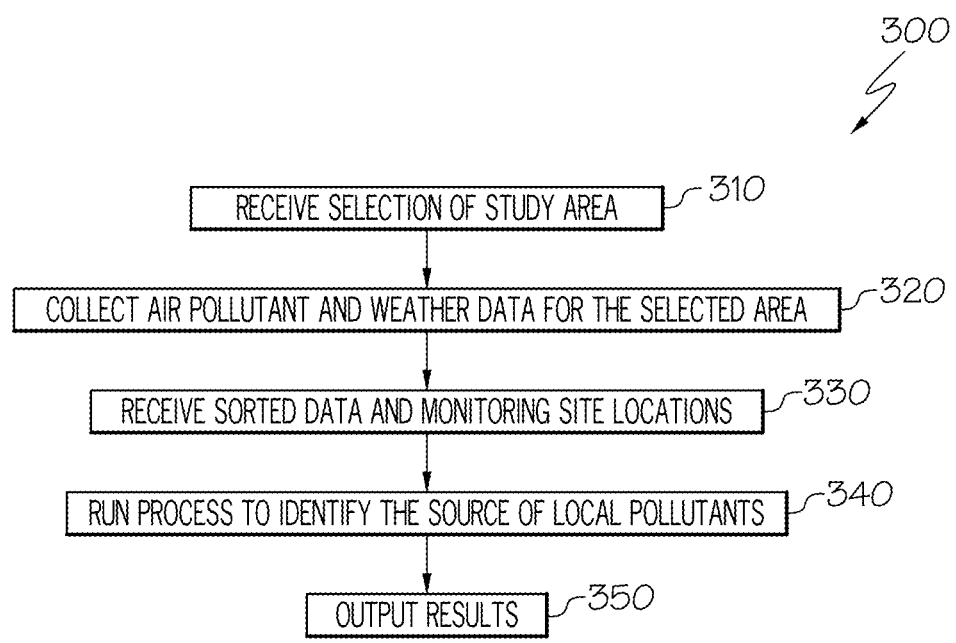
FIG. 3 is a high-level operational flow diagram of the process for net emissions identification, according to an embodiment of the present invention.

FIG. 3—High Level Process Overview

FIG. 3 is an operational flow diagram 300 providing a high-level process overview of the method for identifying net emissions 150, according to an embodiment of the present invention. The process begins at step 310 by selecting a study area. The study area can be, for example, a city, town, region, or province. In one example, the study area is a city with a high API. For purposes of this disclosure, we use the example of Shijiazhuang, a city in the Hebei province of Northern China where air pollution is a growing problem. Once selected, the study area becomes an input to the Extract and Sort Module 251.

After receiving as input the selection of the study area, in step 320 air pollutant data 130 and weather data 140 for the study area (Shijiazhuang) is collected for a predetermined period of time by the Extract and Sort Module 251. The raw data is extracted from databases and then sorted so that the weather data 140 is separate from the air pollution data 130. In step 330 the sorted data and monitoring site information is provided as input to the Grid Size Adaptation module 253 and in step 340 the net emissions identification process continues to determine the source of local pollutants.

Output results 270 are provided in step 350. The output results 270 show the net emissions 150 of air pollutants of a studied area, and finds regions of high levels of air pollution, providing both real-time data and historical data. The output results 270 can take various forms, such as, for example, a heat map 272, a cluster map 274, and/or a trend map 276, to name a few.

Figure 4:
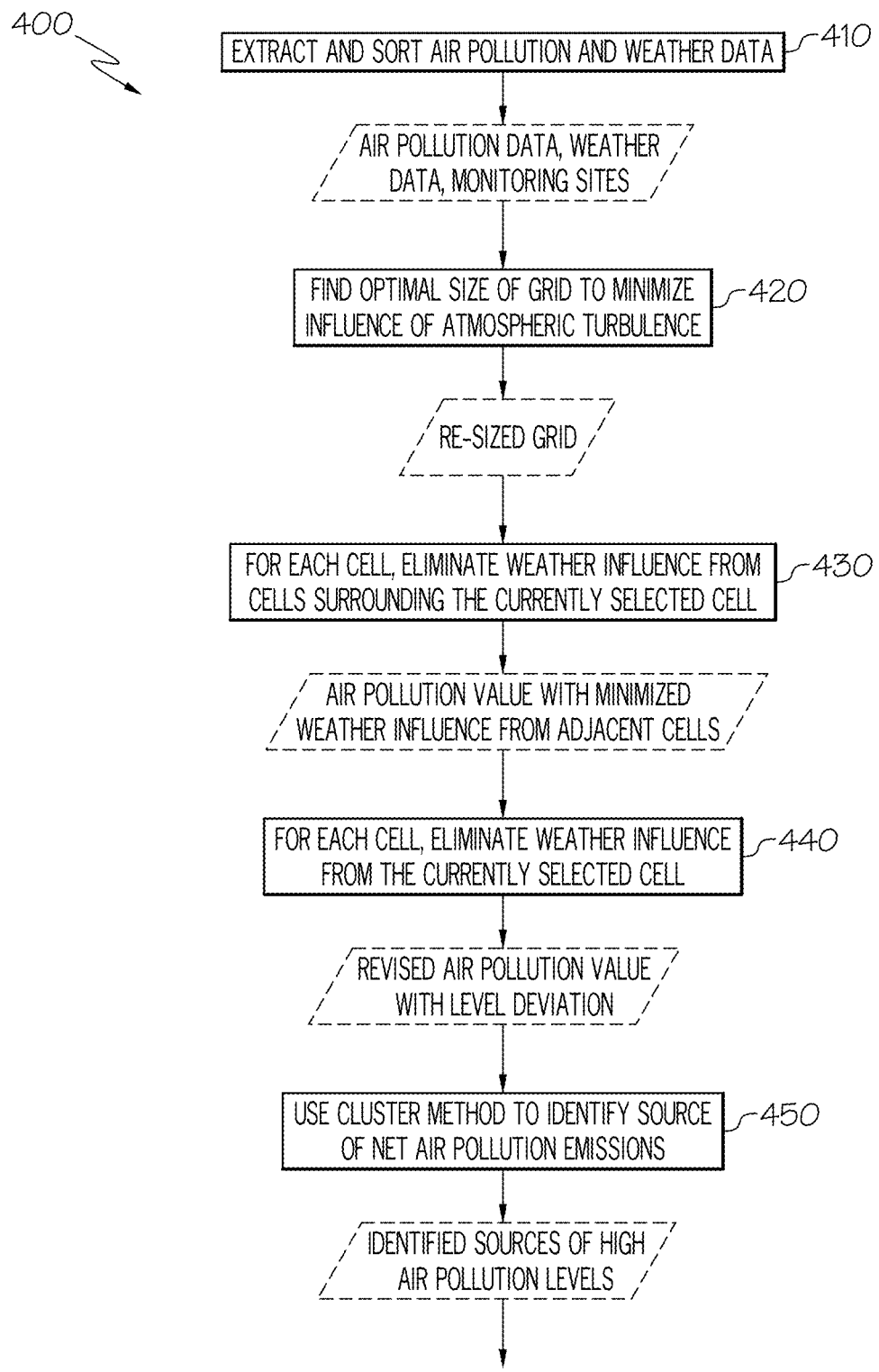
FIG. 4 is an operational flow diagram of the process for evaluating the net emissions of air pollution, according to an embodiment of the present invention.

FIG. 4—Process for Determining the Net Emissions

FIG. 4 is an operational flow diagram 400 of the process for determining the net emissions 150 of air pollutants, according to an embodiment of the present invention. Step 410 is performed by the Extract and Sort Module 251. This step has the following outputs: 1) air pollution values and the locations and identifiers of air quality monitoring sites 112; and 2) weather data and the location and identifiers of weather monitoring sites 116. The remaining steps 420, 430, 440, and 450 are directed to grid analysis and separation of weather conditions 120 from the air pollution concentration value 114, such that what remains is a better calculation of the net emissions 150. Steps 430 and 440 are iteratively performed for each cell in the grid.

Step 420 is the process executed by the Grid Size Adaptation Module 253 to minimize the influence of atmospheric turbulence on the air pollution concentration value 114 by determining an optimal grid size. The output of this process is a re-sized grid.

Step 430 is the process to minimize the weather influence of wind on the cells adjacent to the currently selected cell in the grid by training and fluid dynamics, as executed by the Fluid Dynamics Calculation Module 255. For each cell, the output of this process is a re-calculated air pollution concentration value 114 where the weather influence from the adjacent, or surrounding, cells is minimized.

Step 440 is the process to minimize the weather influence of wind and humidity on the currently selected cell in the grid by training, as executed by the Machine Learning Module 257. For each cell, the output of this process is the re-calculated air pollution concentration value 114 of the previous step 430, revised by a standard deviation.

Step 450 is the process to minimize the diffusion and dispersion factors by using a cluster method to find the true source of the net emissions 150, as executed by the Source Center Location Module 259. The output of this process is a grid marking the sources of high levels of air pollution.

Figure 5:
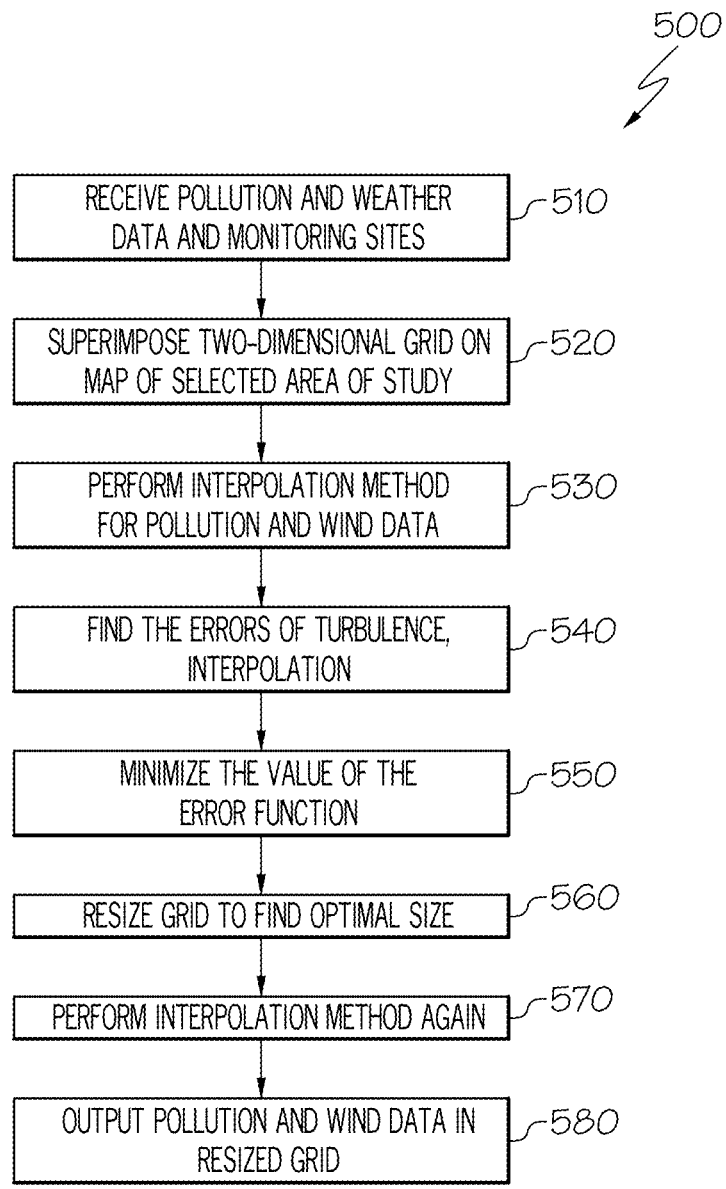
FIG. 5 is an operational flow diagram of the process for finding an optimal grid size, according to an embodiment of the present invention.
Figure 6:
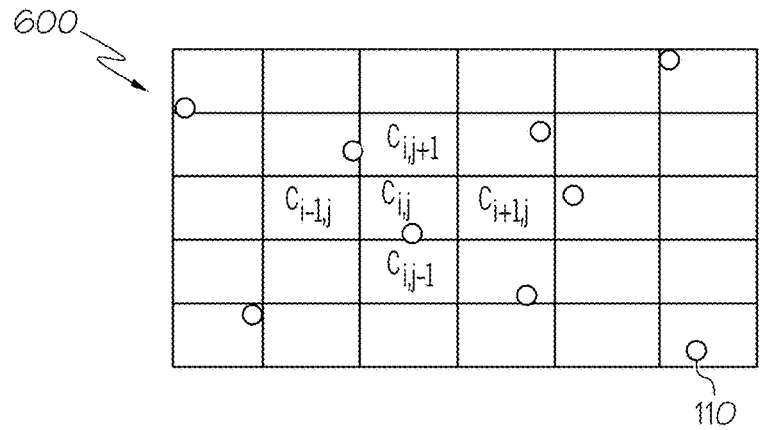
FIG. 6 shows an exemplary two-dimensional grid, according to an embodiment of the present invention.
Figure 7:
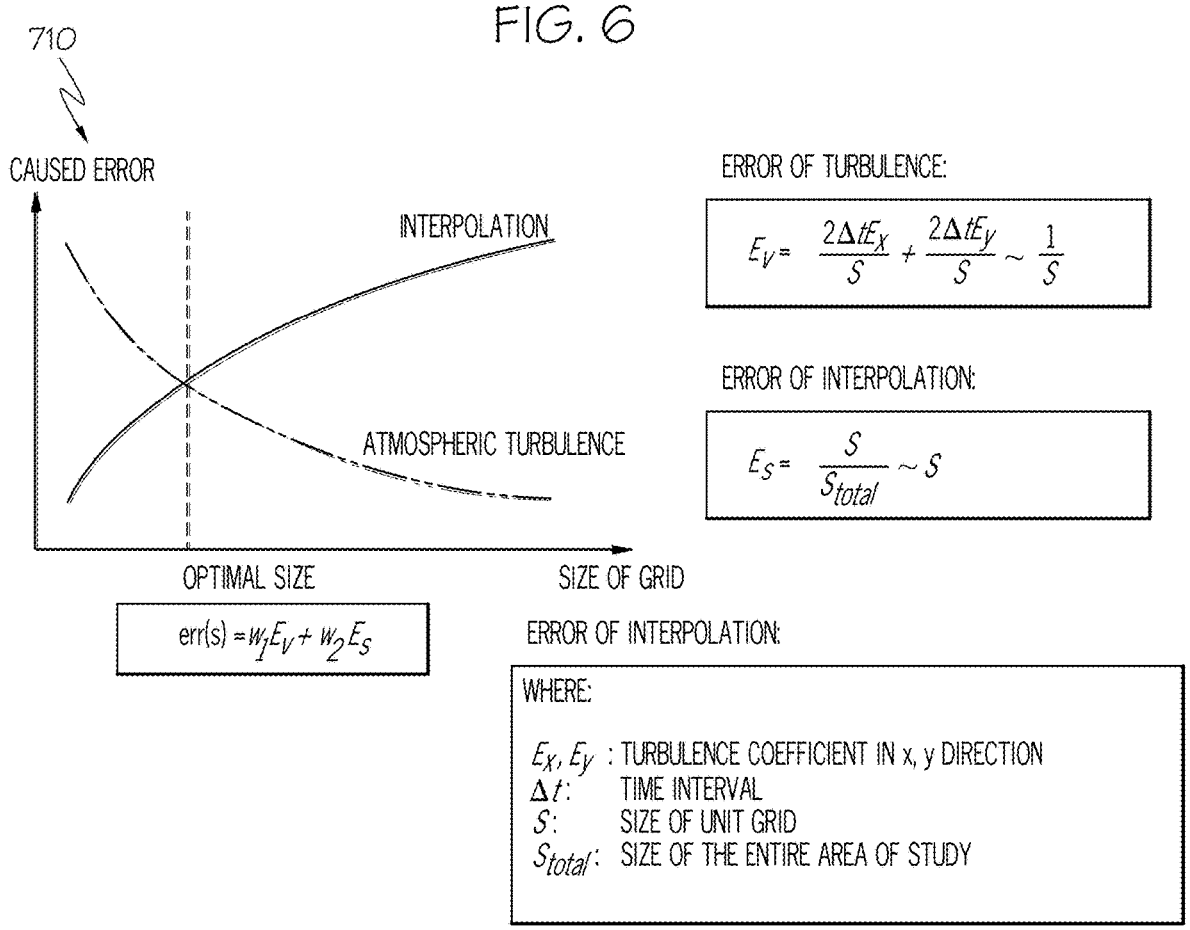
FIG. 7 is a graph showing the relationship between grid size and atmospheric turbulence, according to an embodiment of the present invention.

FIGS. 5, 6, and 7—Finding the Optimal Grid Size

Figure 17:
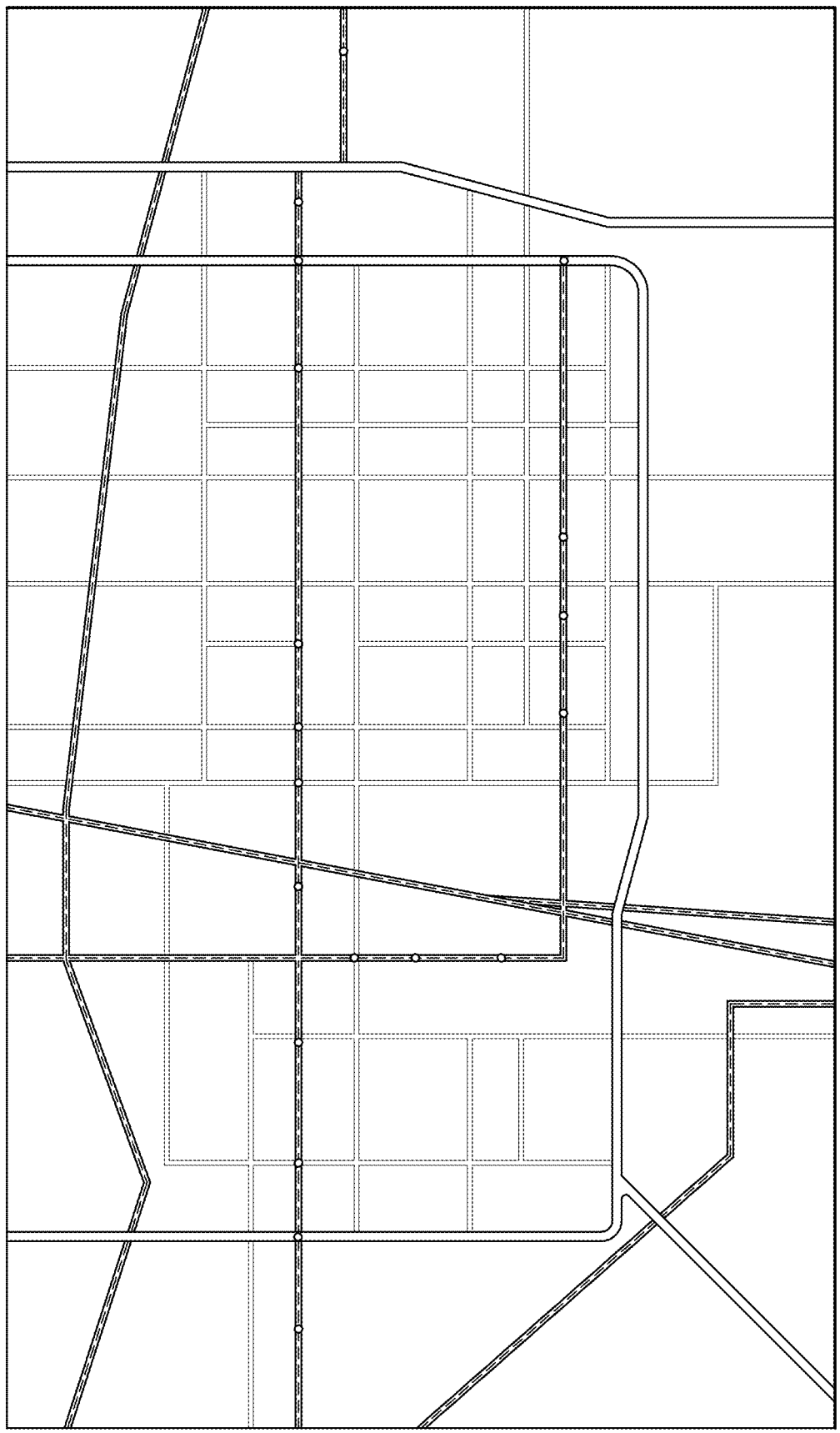
FIG. 17 is a city map of Shijiazhuang in Hebei Province, China.

Referring now to FIG. 5, there is shown an operational flow diagram 500 of the process for finding an optimal grid size, according to an embodiment of the present invention. In one embodiment, the process is executed by the Grid Size Adaptation Module 253 and involves the following steps:

The process begins at step 510 by receiving the outputs from the Extract and Sort Module 251 (the sorted pollution values and weather data and the monitoring sites 110). In step 520 a representation of the selected area, such as a city map of Shijiazhuang City, shown in FIG. 17, is divided into a grid in two-dimensional space. One of the ways in which this can be done is by superimposing a two-dimensional array over a city map. An example of a two-dimensional grid 600 is shown in FIG. 6. In this example, the monitoring sites 110 are designated by dots. The grid size must be carefully selected in order to minimize the influence on the air pollution concentration value 114 attributed to atmospheric turbulence. As a random factor, turbulence cannot be defined by formulas; therefore careful selection of grid size is important.

Because turbulence cannot be adequately measured, we mitigate its influence on the air pollution concentration value 114 by making the size of the grid 600 as large as possible so that the turbulence factor becomes negligible. In other words, as the size of a cell C in the grid 600 increases, the effects of turbulence on the air pollution concentration value 114 for that cell C decreases. The problem is that larger cell sizes means lower calculation accuracy. Therefore, the goal is to find the size of the grid 600 that balances turbulence influence and accuracy.

For each cell C in the grid 600, we collect the air pollution data 130 and weather data 140 from the monitoring sites 110 located within the cell C. It is likely that every grid cell C does not contain a monitoring site 110; therefore in step 530 we use an interpolation method to assign air pollution data 130 and weather data 140 values to those cells that do not contain values explicitly obtained from monitoring sites 110. In this manner the process is able to assign an air pollution concentration value 114 for each grid cell C. For purposes of this discussion, we use the mathematical definition of interpolation as applied to graphical data, i.e., to derive a value in a gap of graphical data by estimating the value from known values surrounding the gap.

For the "gap" cells, we select monitored data from air quality monitoring sites 112 and weather monitoring sites 116 in the range of the gap cells. From that monitored data, we can estimate the air pollution value and wind value of each cell C even if the cell C is a gap cell, i.e., it does not contain a monitoring site 110. We estimate by weighting the monitored data according to distance from the cell C. So for gap cells, we estimate weather and air pollution values according to the gap cell's distance to different monitoring sites 110. We attribute a higher weight to the monitored data closer to the gap cell C because it is likely that the closer a gap cell C is to a monitoring site 110, the more likely it is that the values of the monitored air pollution data 130 and weather data 140 apply to that gap cell C. We know that the interpolation method is not exact and we are working with an estimate; therefore we calculate an error of interpolation in step 540. And because the interpolation method produces more accurate results with a smaller grid size, we use the following formula:

$$E_s = \frac{S}{S_{total}} \sim S$$

where: $E_s$: error of interpolation

In addition to calculating an error of interpolation, we calculate the error of turbulence. In fluid dynamics, the turbulence coefficient is described as a range value which varies under different conditions. To calculate a range value, we first select an average value for a studied area according to statistical analysis. In sizing the grid 600, we need to accommodate two competing factors: 1) the interpolation method produces more accurate results as the grid 600 gets smaller; while 2) atmospheric turbulence causes more errors as the grid 600 gets smaller. The effects of atmospheric turbulence become negligible in a large grid 600. This can be expressed by the following formula:

$$E_v = \frac{2\Delta t E_x}{S} + \frac{2\Delta t E_y}{S} \sim \frac{1}{s}$$

where:
$E_x$, $E_y$: turbulence coefficient in x, y direction.
$\Delta t$: time interval
S: size of cell
$S_{total}$: size of the whole studied area (size of grid 600)
$E_v$: error of turbulence The turbulence coefficient is a calculated value related to the average wind value, mean square wind value. We estimate the turbulence coefficient using an empirical equation from fluid dynamics, a time average value, as follows:

First, we calculate the Lagrange correlation coefficient R, expressed as $$R_L: R_L(\tau) = \frac{\overline{V(x, \tau)V(x, t_0)}}{\overline{V^2}},$$

where:
$\tau$ is the time point in range $(t_0, t_{end})$,
V is wind velocity in x or y direction of a studied cell C, and
$\overline{V^2}$ is the mean squared value of V.

Second, we calculate $T_L$: $T_L = \int_{t_0}^{t_{end}} R_L(\tau) \, d\tau$. In one embodiment, the time period between $t_0$ and $t_{end}$ is selected as 24 hours to estimate the $T_L$ value, meaning that the calculation frequency of the coefficient is daily. Third, we then calculate the turbulence coefficient in the x or y direction as $E = \overline{V^2} T_L$. After we calculate the turbulence coefficient for x and y ($E_x$, $E_y$) for each weather monitoring site 116, we use this as an average value. This average value is used to designate the studied area's turbulence coefficient of that day.

In step 550 we minimize the value of the error function using the following formula:

errs(s)=$w_1 E_v + w_2 E_s$ where w stands for the weight factors assigned to the error function results, $E_v$ and $E_s$, such that $w_1 + w_2 = 1$. We set the weight factors according to the importance of the two function results. The weight factors $w_1$ and $w_2$ both default to 0.5, signifying that the two error results are of the same importance.

Figure 9:
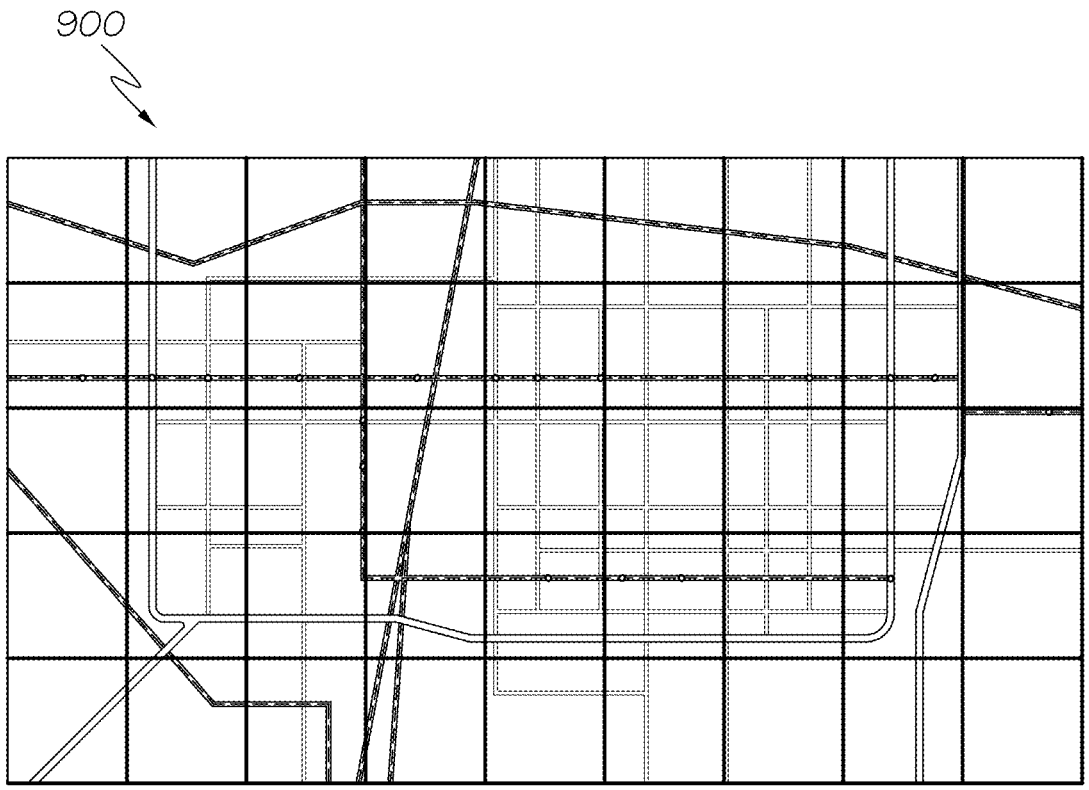
FIG. 9 shows an example of a re-sized grid overlaid over an area of study, according to an embodiment of the present invention.

According to one embodiment, we chart the values by plotting two lines of points. The optimal size of the grid 600 is the intersection of the two lines of points, representing the two competing factors: interpolation and turbulence, on a graph, such as the graph 710 shown in FIG. 7. In step 560 we re-size the cells in the grid 600 to the optimal size determined in step 550. FIG. 9 shows an example of a re-sized grid 900. In step 570 we perform the interpolation method again on the re-sized grid 900 so that we acquire interpolation results of cells from the re-sized grid 900. In step 580 we output the air pollution data 130 and weather data 140 for each cell C in the newly-sized grid 900.

Figure 8:
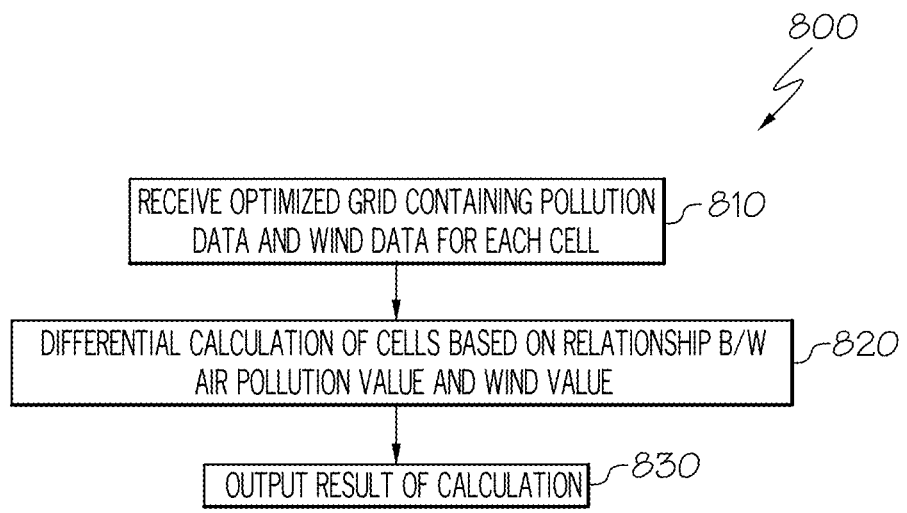
FIG. 8 is an operational flow diagram of the process for minimizing the weather influence from outer cells of the grid, according to an embodiment of the present invention.

FIG. 8—Eliminate Weather Influence from Adjacent Cells

Referring now to FIG. 8, there is shown an operational flow diagram 800 of the process for eliminating weather influence from adjacent cells in the re-sized grid 900. The adjacent cells are the four cells surrounding the currently selected cell C. These are the cells immediately above and below cell C and immediately to the right and left of cell C. For example, referring now to the grid 600 shown in FIG. 6, assume the selected cell is cell $C_{i,j}$. The adjacent cells are $C_{i,j+1}$, $C_{i-1,j}$, $C_{i+1,j}$, and $C_{i,j-1}$. For purposes of this discussion, we will refer to the cell that is currently being examined as $C_{i,j}$.

In step 810 the input to the Fluid Dynamics Calculation module 255 is the newly-sized grid 900 containing air pollution values and weather values for each grid cell $C_{i,j}$ in the newly-sized grid 900. We assume that the values for each grid cell $C_{i,j}$ are related to its four adjacent cells, and the same cell $C_{i,j}$ of a previous time point. The data from each cell $C_{i,j}$ is monitored at pre-determined time intervals, such as every hour. For example, for a one-hour time interval, if the current time point is 8 o'clock, the previous time point is 7 o'clock. We obtain the value of each cell $C_{i,j}$ and its four adjacent cells $C_{i-1,j}$, $C_{i+1,j}$, $C_{i,j-1}$, $C_{i,j+1}$ for a total of five total cells, at 8 o'clock and also the value of this cell $C_{i,j}$ at 7 o'clock.

Figures 10, 11:
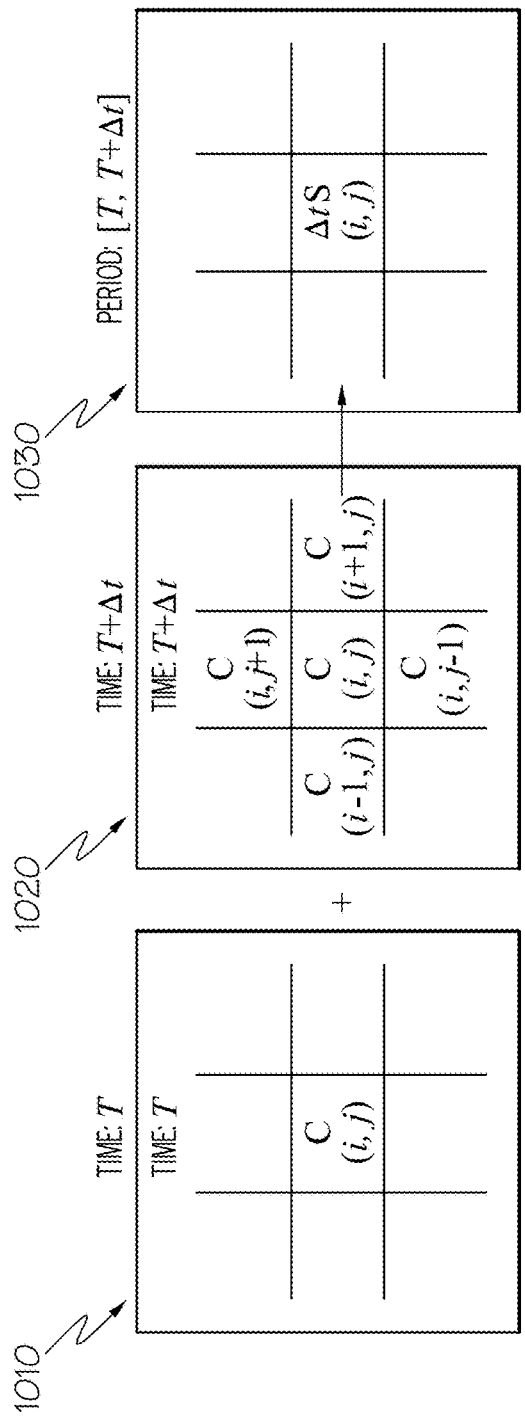
FIG. 10 shows a time sequence model of the relationship among cells in the grid, according to an embodiment of the present invention.
FIG. 11 shows the formula for determining the weather influence from outer cells in the grid, according to an embodiment of the present invention.

In step 820, for each grid cell $C_{i,j}$ we use fluid dynamics to perform a differential calculation of grid cells based on the relationship between the air pollution concentration value 114 and weather factors, such as wind. Referring now to FIG. 10, the above calculation is graphically shown. In graph 1010, for each cell $C_{i,j}$ at time=T we obtain the cell's values and then the values of its four adjacent cells, for time=T and the pre-defined time interval ΔT, in graph 1020. The influence from the adjacent cells is taken into consideration in the equation of FIG. 10. The right part of the equation is related to the air pollution concentration value 114 of the selected cell $C_{i,j}$ and its four adjacent cells, but the result S(i,j) is only related to the selected cell $C_{i,j}$. Therefore, we eliminate the influence of each adjacent cell using this equation. The equation provides the S(i,j) for each cell. There still remains, however, a weather factor affecting the air pollution value in the selected cell $C_{i,j}$. We label it as "weather influence from selected cell," and will minimize it in next part in FIG. 12 as "Err(L)."

Once we obtain the air pollution values, we perform a calculation based on fluid dynamics (shown in FIG. 11) to arrive at a re-calculated air pollution value for that cell $C_{i,j}$, shown in graph 1030, after mitigating the weather influence from the adjacent cells. In step 840 we output the results of the differential calculation, the re-calculated air pollution for cell $C_{i,j}$.

Figure 12:
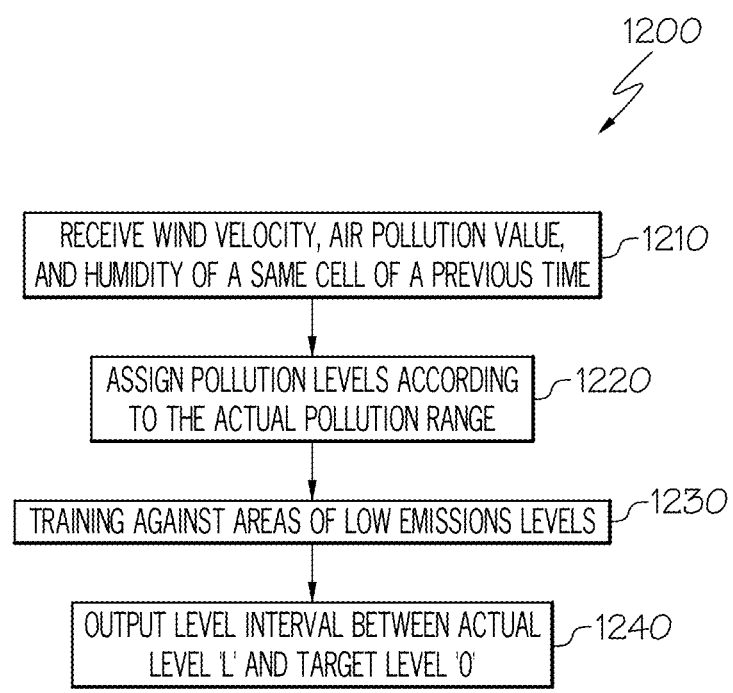
FIG. 12 is an operational flow diagram of the process for minimizing the weather influence from inner cells of the grid, according to an embodiment of the present invention.

FIG. 12—Minimize Weather Influence from Selected Cell

Referring now to FIG. 12, there is shown an operational flow diagram 1200 of the process for minimizing the weather influence from the re-calculated air pollution value in the currently selected cell $C_{i,j}$ of the re-sized grid 900, according to an embodiment of the present invention. In step 1210 the inputs to the process are: the re-calculated air pollution value, wind velocity, and humidity of a same grid 900 or grid cell $C_{i,j}$ from a previous time. These input values represent a "rough" net emission value for the cell $C_{i,j}$ in the re-sized grid 900. It is only a "rough" estimate because we still need to eliminate an approximation of the weather factors from the cell $C_{i,j}$ in the grid 900.

We know that the re-calculated air pollution value is influenced by wind and humidity from the cell $C_{i,j}$. Humidity is only a mitigating factor for the currently selected cell $C_{i,j}$, while wind is relevant to both this cell $C_{i,j}$ and its adjacent cells. The residual factor after eliminating the weather influence from the adjacent cells is expressed as: f(c,v,h), where c is the re-calculated air pollution value, v is the wind value, and h is the humidity value.

In order to achieve a normalization of the net emission result, in step 1220 the re-calculated air pollution value is converted to an air pollution level by assigning an air pollution level to the cells in the grid 900 according to the actual air pollution range. For example, assume the range of values for air pollution is measured from 0 to 500, and there are 11 levels from "Level 1" to "Level 11." The air pollution value between 0 and 50 is classified as Level 1 (in the "Good" range), the value between 50 and 100 is classified as Level 2, . . . and so on. According to this system, if the air pollution value is 120, it is classified as Level 3. In this way, the continuous variables are transformed to a fixed number of discrete variables, which can be classified by machine learning: L={0, 1, 2, . . . ,}, where L=level.

There still remains a mitigating factor related to the group parameters of wind and humidity with respect to the re-calculated air pollution value from the currently selected cell $C_{i,j}$ which cannot be expressed by fluid dynamics. In step 1230 we mitigate the influence from those factors by applying machine learning to eliminate the influence of wind and humidity in the cell $C_{i,j}$. Training and testing datasets are selected from special areas such as forests or water where the expected net emission level is substantially zero, i.e., L=0. In an off-line process, we train on grids of these special areas, for a selected period of time to produce training data with expected results. However, the actual air pollution level assigned to cell $C_{i,j}$ may be higher than 0. To express this deviation from the training data, we assign the level interval (the deviation) between the actual level L and the expected level 0 as Err(L). For example, if the actual air pollution level is 3 (L=3), and the expected level L=0, the deviation can be stated as Err(L)=3. Using that deviation value, we can build the relationship between Err(L) and the group parameters of the re-calculated air pollution value, wind, and humidity.

To build the relationship, in one embodiment we first build a deep neural network (DNN) model. The DNN has one input layer, one output layer, and several hidden layers. The DNN receives as input data: the re-calculated air pollution value, wind velocity, and humidity (c, v, h); and the output data is Err(L). The input data is collected from special areas such as forests or water to train and test the model. Once the model is sufficiently trained, it is applied to the area of study.

Figure 13:
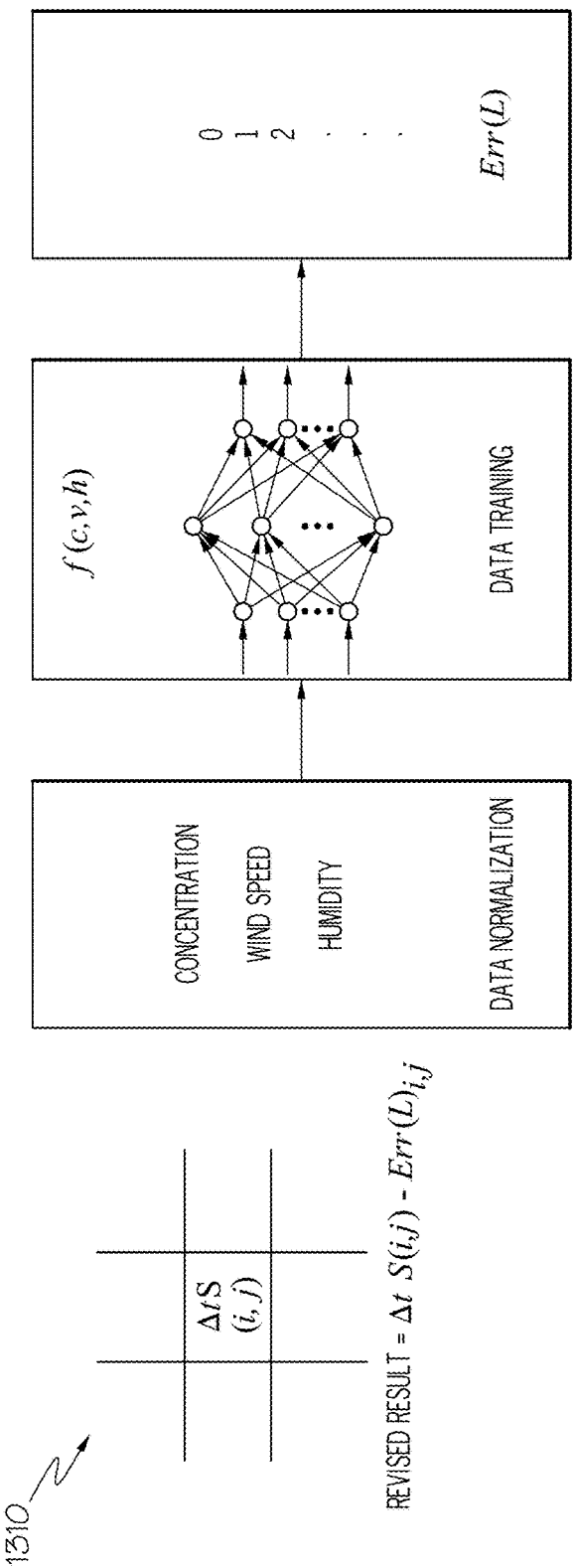
FIG. 13 shows a conceptual diagram of the use of training data to minimize the weather influence from inner cells of the grid, according to an embodiment of the present invention.

In step 1240 we output Err(L)—the deviation between the actual air pollution level 'L' of each cell $C_{i,j}$ and the training or target level. FIG. 13 shows a conceptualization of using machine learning to minimize the weather influence from cell $C_{i,j}$ of the grid 900, according to an embodiment of the present disclosure. Going back to FIG. 10, graph 1030, where we calculated the air pollution value for the cell $C_{i,j}$ as $\Delta t S_{i,j}$ we now have a revised result as a result of applying machine learning. As graph 1310 shows, the revised air pollution value for the cell is: $\Delta t \times S(i,j) - \text{Err}(L)_{i,j}$.

Figure 14:
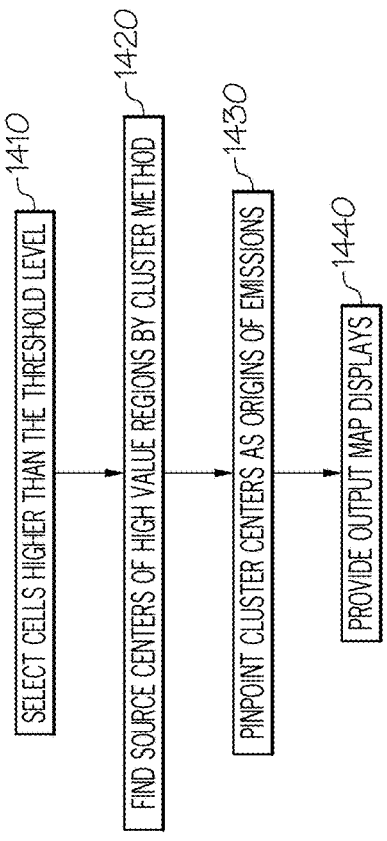
FIG. 14 is an operational flow diagram of the process for finding source centers of high air pollution levels using the cluster method, according to an embodiment of the present invention.
Figure 15:
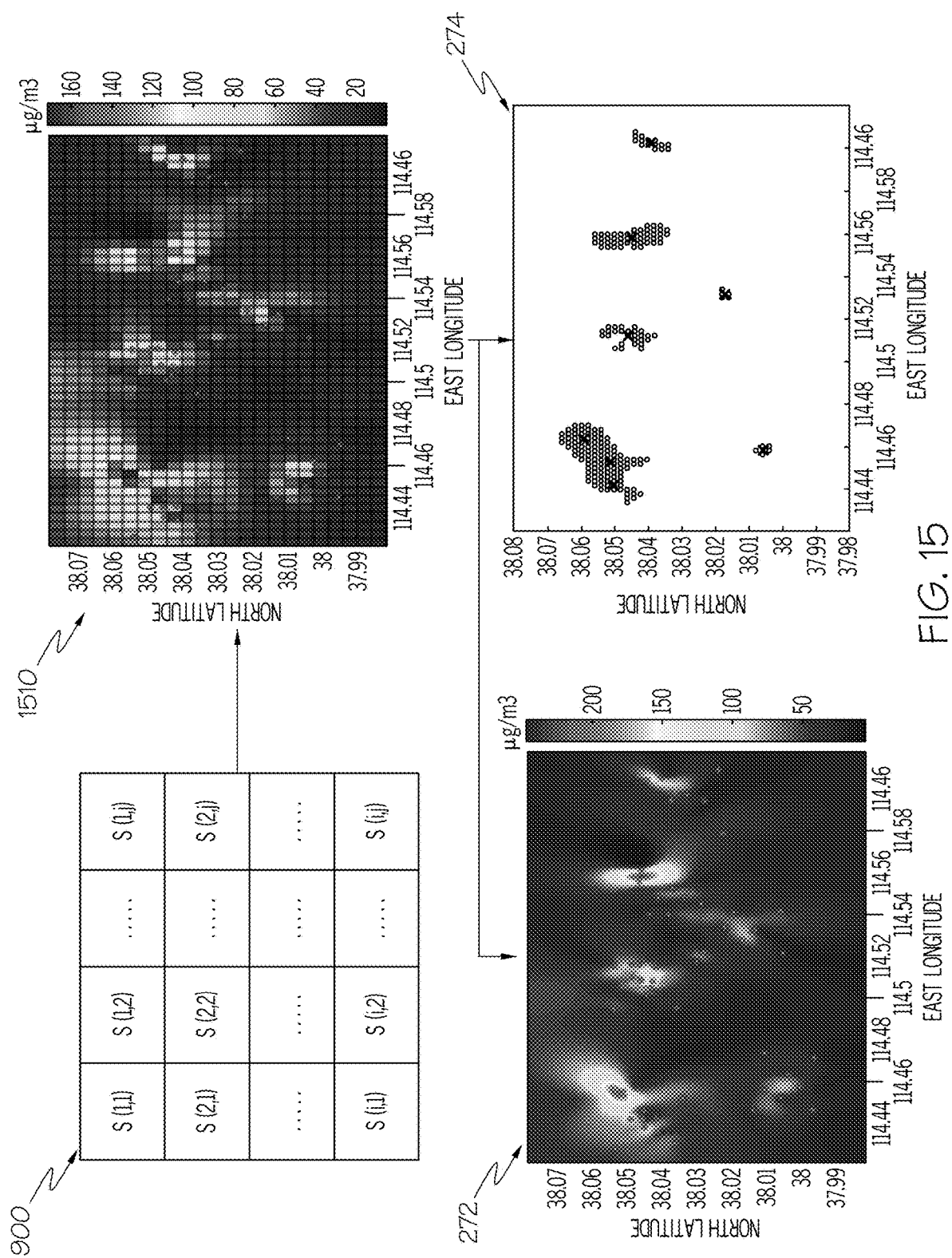
FIG. 15 shows the output after applying the cluster method, according to an embodiment of the present invention.

FIGS. 14 and 15—Cluster Method

Referring now to FIG. 14, there is shown an operational flow diagram 1400 of the cluster method for identifying the sources of high levels of air pollution 130, according to an embodiment of the present disclosure. In step 1410 the cells containing air pollution levels which are higher than a pre-determined threshold level are selected. The selected cells can be visually distinguished, as in the enhanced grid 1510 shown in FIG. 15. For example, assuming the threshold level of air pollution 130 is two, all of the cells with air pollution levels greater than two are selected. In step 1420, focusing on only those cells with air pollution levels greater than the threshold, the cluster method is applied to highlight the source centers of high levels of air pollution 130. This can be graphically presented in various forms, such as a heat map 272 or a cluster map 274.

In step 1430 the position of the center of each cluster from step 1420 can be regarded as the origin, or source, of the net emissions 150. Lastly, in step 1440 we provide graphical illustrations highlighting the regions of high levels of air pollution 130. This can be presented as a heat map 272. Using a cluster map 274 we can visually pinpoint the cluster centers as the location source of net emissions 150. The "Xs" in cluster map 274 mark the location sources of net emissions 150. This identification of the source of net emissions 150 provides valuable information in the ongoing effort to control air pollution 130.

Figure 16:
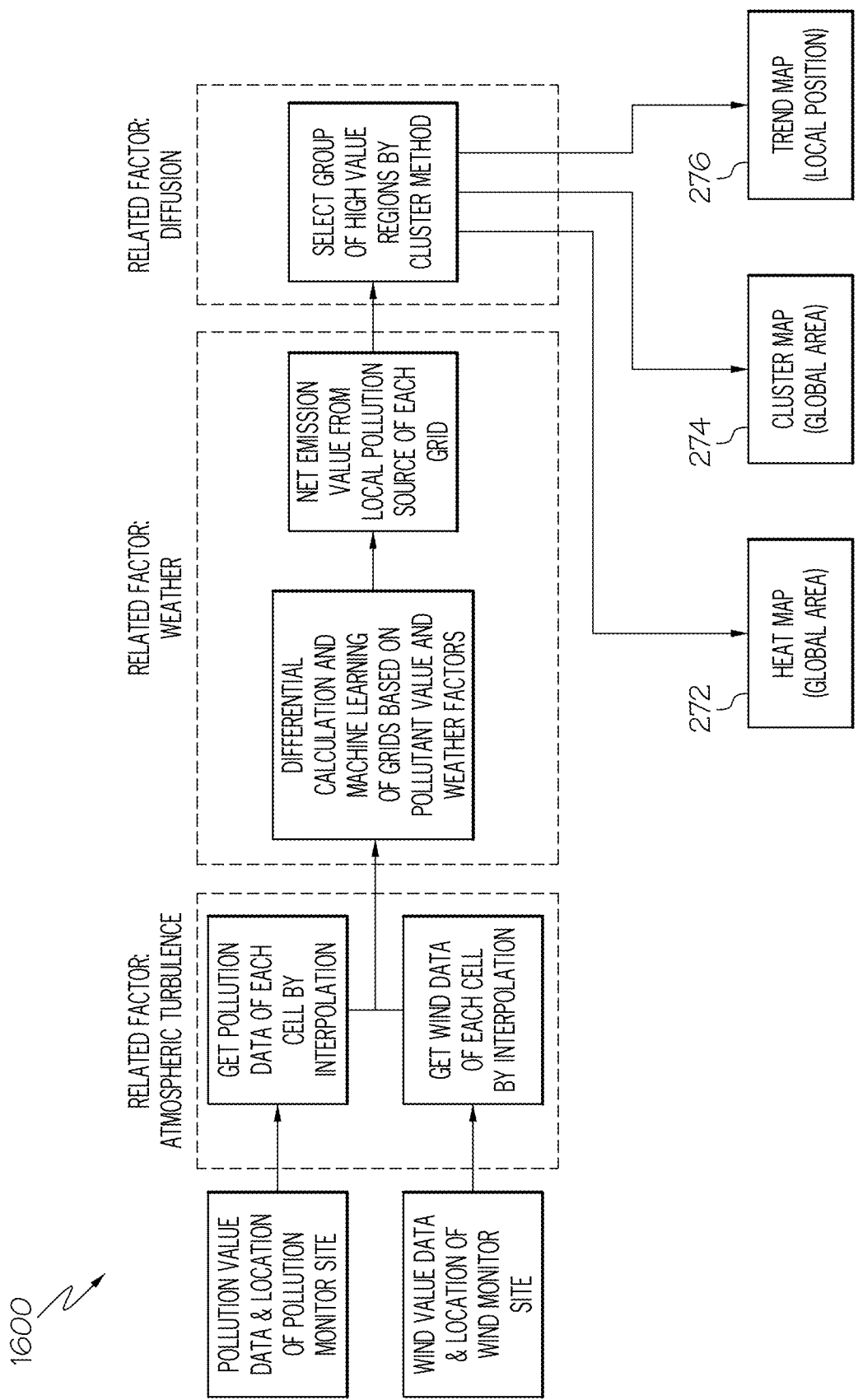
FIG. 16 is a system chart showing the different processes grouped according to the weather factor they target for minimization, according to an embodiment of the present invention.

FIG. 16 System Chart

FIG. 16 is a system chart 1600 showing the different processes grouped according to the weather factor they target for minimization, according to an embodiment of the present disclosure.

FIG. 17—City Map

FIG. 17 shows a map of Shijiazhuang City in Hebei Province, China. It is the same scale of the graphical representation area in FIG. 9.

Figure 18A:
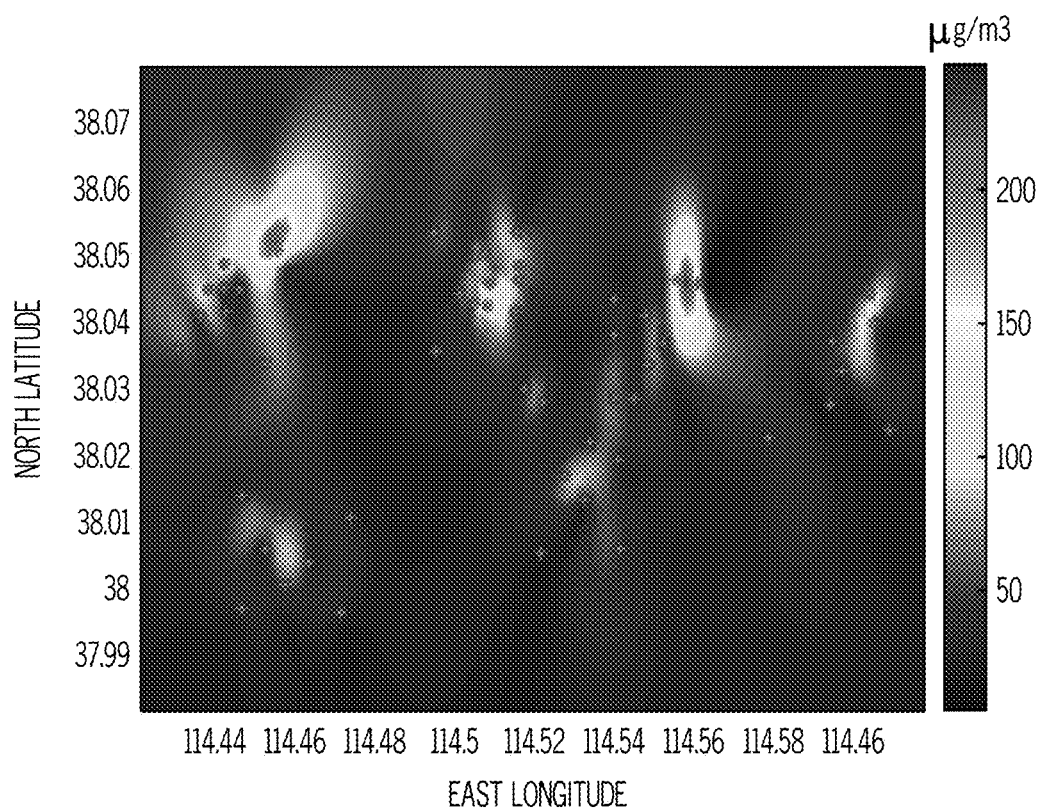
FIG. 18A is a heat map showing areas of high air pollution levels, according to an embodiment of the present invention.
Figure 18B:
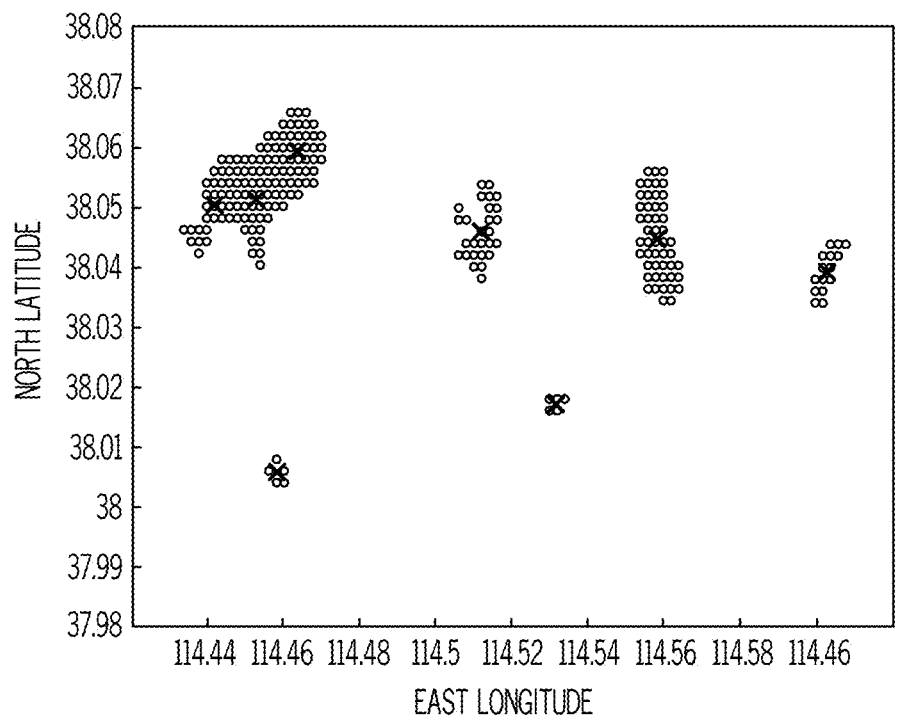
FIG. 18B is a cluster map pinpointing source centers of high air pollution levels, according to an embodiment of the present invention.
Figure 18C:
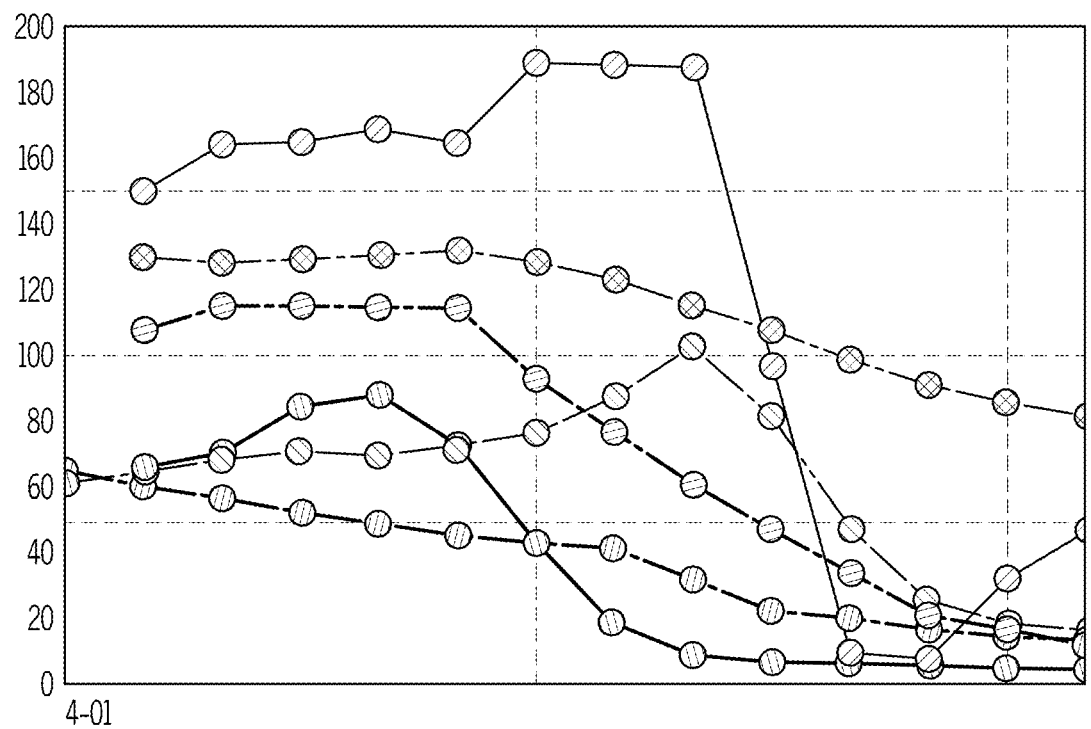
FIG. 18C is a trend map showing net emission levels over a period of time, according to an embodiment of the present invention.

FIGS. 18A, 18B, and 18C—Map Results

FIGS. 18A, 18B, and 18C show some examples of outputs 270 from the process of identifying net emissions 150. FIG. 18A shows an example of a heat map 272 illustrating the areas of high levels of air pollution 130. In the heat map 272 the levels are represented by colors, with blue designating an area of good air quality and red designating an area of poor air quality. FIG. 18B shows a cluster map 274 pinpointing the location sources of net emissions 150 using Xs. FIG. 18C shows a trend map 276 of the air pollution levels over time.

Figure 19:
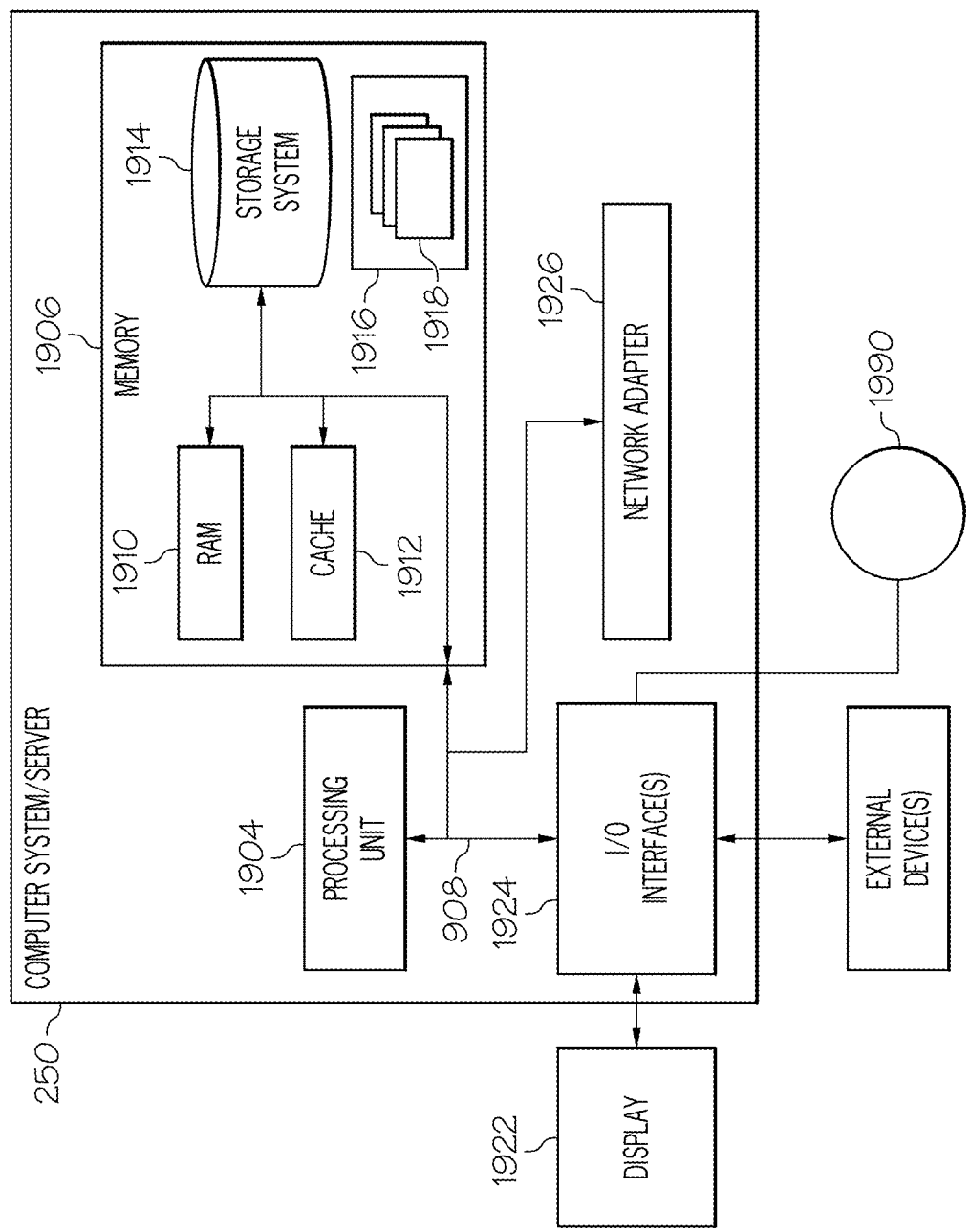
FIG. 19 shows a simplified block diagram of an information processing system for tuning machine learning systems, according to embodiments of the present invention.

FIG. 19—Hardware Embodiment

FIG. 19 illustrates one example of the components of an information processing system 1900 for identifying sources of high levels of air pollution that can be utilized in various embodiments of the present invention. The information processing system 1900 shown in FIG. 19 is only one example of a suitable system and is not intended to limit the scope of use or functionality of embodiments of the present invention described above. The information processing system 1900 of FIG. 19 is capable of implementing and/or performing any of the functionality set forth above. Any suitably configured processing system can be used as the information processing system 1900 in embodiments of the present invention.

The information processing system 1900 is operational with numerous other general purpose or special purpose computing system environments or configurations. Examples of well-known computing systems, environments, and/or configurations that may be suitable for use with the information processing system 1900 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The information processing system 1900 may be described in the general context of computer-executable instructions, being executed by a computer system. The information processing system 1900 may be practiced in various computing environments such as conventional and distributed cloud computing environments where tasks are performed by remote processing devices that are linked through a communications network. In a distributed cloud computing environment, program modules may be located in both local and remote computer system storage media including memory storage devices.

As illustrated in FIG. 19, the information processing system 1900 includes the Net Emissions Identifier 250 in the form of a general-purpose computing device. The components of the Net Emissions Identifier 250 can include, but are not limited to, one or more processor devices or processing units 1904, a system memory 1906, and a bus 1908 that couples various system components including the system memory 1906 to the processor 1904.

The bus 1908 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 1906 can also include computer system readable media in the form of volatile memory, such as random access memory (RAM) 1910 and/or cache memory 912. The Net Emissions Identifier 250 can further include other removable/non-removable, volatile/non-volatile computer system storage media. By way of example only, a storage system 1914 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 1908 by one or more data media interfaces. The memory 1906 can include at least one program product having a set of program modules that are configured to carry out the functions of an embodiment of the present invention.

Program/utility 1916, having a set of program modules 1918, may be stored in memory 1906 by way of example, and not limitation, as well as an operating system, one or more application programs, other program modules, and program data. Generally, program modules may include routines, programs, objects, components, logic, data structures, and so on that perform particular tasks or implement particular abstract data types. Each of the operating system, one or more application programs, other program modules, and program data or some combination thereof, may include an implementation of a networking environment. Program modules 1918 generally carry out the functions and/or methodologies of embodiments of the present invention.

The Net Emissions Identifier 250 can also communicate with one or more external devices 1920 such as a keyboard, a pointing device, a display 1922 presenting, for example, a heat map 272, cluster map 274, and trend map 276; one or more devices that enable a user to interact with the Net Emissions Identifier 250; and/or any devices (e.g., network card, modem, etc.) that enable the Net Emissions Identifier 250 to communicate with one or more other computing devices. Such communication can occur via I/O interfaces 1924. Still yet, the Net Emissions Identifier 250 can communicate with one or more networks such as a local area network (LAN), a general wide area network (WAN), and/or a public network (e.g., the Internet) via network adapter 1926, enabling the system 1900 to access data from monitoring sites 110. As depicted, the network adapter 1926 communicates with the other components of the Net Emissions Identifier 250 via the bus 1908. Other hardware and/or software components can also be used in conjunction with the Net Emissions Identifier 250. Examples include, but are not limited to: microcode, device drivers, redundant processing units, external disk drive arrays, RAID systems, tape drives, and data archival storage systems.

Computer Program Product Support

As will be appreciated by one skilled in the art, aspects of the present invention may be embodied as a system, method, or computer program product 1990 at any possible technical detail level of integration. The computer program product may include a computer readable storage medium 1990 (or media) having computer readable program instructions thereon for causing a processor to carry out aspects of the present invention.

Any combination of one or more computer readable medium(s) may be utilized. The computer readable storage medium 1990 can be a tangible device that can retain and store instructions for use by an instruction execution device. The computer readable storage medium 1990 may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium 1990 includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium 1990, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Accordingly, aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

A computer readable signal medium may include a propagated data signal with computer readable program code embodied therein, for example, in baseband or as part of a carrier wave. Such a propagated signal may take any of a variety of forms, including, although not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer readable program instructions described herein can be downloaded to respective computing/processing devices from a computer readable storage medium 1990 or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention have been discussed above with reference to flowchart illustrations and/or block diagrams of methods, apparatus (systems) and computer program products according to various embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a non-transitory computer readable storage medium that can direct a computer, other programmable data processing apparatus, or other devices to function in a particular manner, such that the instructions stored in the computer readable medium 1990 produce an article of manufacture including instructions which implement the functions/acts specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, although do not preclude the presence or addition of one or more other features, integers, steps, operations, elements, components, and/or groups thereof.

NON-LIMITING EXAMPLES

The description of the present application has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. A computer-implemented method for determining a location source of pollutant emissions in a selected area, the computer-implemented method comprising:
   receiving monitoring data collected from at least one monitoring site in the selected area, the monitoring data collected over a predetermined period of time, wherein the monitoring data comprises air pollution data and weather data for a section of the selected area;
   mapping a grid onto a representation of the selected area;
   wherein at least one cell in the grid represents the section of the selected area encompassing the at least one monitoring site;
   wherein at least one cell in the grid is a gap cell that does not encompass the at least one monitoring site;
   assigning an air pollution value and a weather value from the monitoring data to each cell in the grid;
   generating a re-sized grid by re-sizing cells in the grid to minimize an influence attributed to atmospheric turbulence on an air pollution value assigned to each of the cells;
   for each cell in the re-sized grid, eliminating an approximation of a weather influence from the air pollution value assigned to a selected cell by obtaining the selected cell's monitoring data for a time $T+\Delta T$ and a previous time T and obtaining the monitoring data for the cells adjacent to the selected cell for a time $T+\Delta T$ and a previous time T;
   using a machine learning technique to minimize an influence of wind speed and humidity in the selected cell in which the approximation of the weather influence has been eliminated, the machine learning technique using datasets trained in locations where an expected net emissions level is substantially zero, and outputting a deviation between a training level of air pollution and an actual air pollution level;

using a cluster method to find a source center of a region with high levels of pollutant emissions to approximate an influence attributed to diffusion; and providing results showing the location source of the pollutant emissions.

2. The computer-implemented method of claim 1 wherein mapping the grid comprises mapping locations from the selected area onto a two-dimensional grid.

3. The computer-implemented method of claim 1 wherein re-sizing cells in the grid comprises:

using an interpolation method to assign the air pollution value and the weather value to each gap cell;

determining an error of interpolation;

graphing a first line of points of first errors attributed to the interpolation method, wherein decreasing a size of the cells produces more accurate results using the interpolation method;

graphing a second line of points of second errors attributed to the influence of the atmospheric turbulence, wherein increasing the size of the cells minimizes the influence of the atmospheric turbulence;

selecting an optimal size of the cells as an intersection of the first line of points and the second line of points; and repeating the interpolation method to assign values to the re-sized grid.

4. The computer-implemented method of claim 3 wherein using the interpolation method comprises estimating the air pollution value and the weather value for each gap cell by selecting the air pollution data and the weather data from the monitoring sites in cells near each gap cell.

5. The computer-implemented method of claim 4 further comprising weighting the air pollution data and the weather data according to distance to the gap cell, wherein the monitored data from monitoring sites closest to the gap cell are assigned a higher weight.

6. The computer-implemented method of claim 1 further comprising minimizing the weather influence from cells adjacent to the selected cell using fluid dynamics calculations, resulting in a re-calculated air pollution value for the selected cell.

7. The computer-implemented method of claim 6 further comprising converting the re-calculated air pollution value for the cell to an air pollution level within a range of documented air pollution levels, to transform the air pollution value to a discrete variable which can be classified by machine learning.

8. The computer-implemented method of claim 6 further comprising using a cluster method to identify the concentrations of the high levels of the pollutant emissions for the selected area.

9. The computer-implemented method of claim 1 wherein using the machine learning technique comprises training on a deep neural network.

10. An information processing system for determining a location source of pollutant emissions for a selected area, the information processing system comprising:

a processor device; and a memory operably coupled with the processor device and storing computer-executable instructions causing a computer to perform:

receiving monitoring data collected from at least one monitoring site in the selected area, the monitoring data collected over a predetermined period of time, wherein the monitoring data comprises air pollution data and weather data for a section of the selected area;

mapping a grid onto a representation of the selected area;

wherein at least one cell in the grid represents the section of the selected area encompassing the at least one monitoring site;

wherein at least one cell in the grid is a gap cell that does not encompass the at least one monitoring site;

assigning an air pollution value and a weather value from the monitoring data to each cell in the grid;

generating a re-sized grid by re-sizing cells in the grid to minimize an influence attributed to atmospheric turbulence on an air pollution value assigned to each of the cells;

for each cell in the re-sized grid, eliminating an approximation of a weather influence from the air pollution value assigned to a selected cell by obtaining the selected cell's monitoring data for a time $T+\Delta T$ and a previous time $T$ and obtaining the monitoring data for the cells adjacent to the selected cell for a time $T+\Delta T$ and a previous time $T$;

using a machine learning technique to minimize an influence of wind speed and humidity in the selected cell in which the approximation of the weather influence has been eliminated, the machine learning technique using datasets trained in locations where an expected net emissions level is substantially zero, and outputting a deviation between a training level of air pollution and an actual air pollution level;

using a cluster method to find a source center of a region with high levels of pollutant emissions to approximate an influence attributed to diffusion; and providing results showing the location source of the pollutant emissions.

11. The information processing system of claim 10 further comprising a database storing the monitoring data.

12. The information processing system of claim 10 wherein the computer-executable instructions for re-sizing the cells in the grid further comprise an interpolation method to assign the air pollution value and the weather value to each gap cell.

13. The information processing system of claim 12 further comprising minimizing the weather influence from cells adjacent to the selected cell using fluid dynamics calculations, resulting in a re-calculated air pollution value for the selected cell wherein the computer-executable instructions further comprise converting the re-calculated air pollution value for the cell to an air pollution level within a range of documented air pollution levels, to transform the air pollution value to a discrete variable which can be classified by machine learning.

14. The information processing system of claim 10 wherein mapping the grid comprises mapping locations from the selected area onto a two-dimensional grid.

15. The information processing system of claim 10 wherein re-sizing cells in the grid comprises:

using an interpolation method to assign the air pollution value and the weather value to each gap cell;

determining an error of interpolation;

graphing a first line of points of first errors attributed to the interpolation method, wherein decreasing a size of the cells produces more accurate results using the interpolation method;

graphing a second line of points of second errors attributed to the influence of the atmospheric turbulence, wherein increasing the size of the cells minimizes the influence of the atmospheric turbulence;

selecting an optimal size of the cells as an intersection of the first line of points and the second line of points; and repeating the interpolation method to assign values to the re-sized grid.

16. The information processing system of claim 15 wherein using the interpolation method comprises estimating the air pollution value and the weather value for each gap cell by selecting the air pollution data and the weather data from the monitoring sites in cells near each gap cell.

17. The information processing system of claim 16 further comprising weighting the air pollution data and the weather data according to distance to the gap cell, wherein the monitored data from monitoring sites closest to the gap cell are assigned a higher weight.

18. The information processing system of claim 10 further comprising minimizing the weather influence from cells adjacent to the selected cell using fluid dynamics calculations, resulting in a re-calculated air pollution value for the selected cell.

19. The information processing system of claim 18 further comprising converting the re-calculated air pollution value for the cell to an air pollution level within a range of documented air pollution levels, to transform the air pollution value to a discrete variable which can be classified by machine learning.

20. A computer program product for determining a location source of pollutant emissions, the computer program product comprising:

a non-transitory computer readable storage medium readable by a processing device and storing instructions for execution by the processing device for performing a method comprising:

receiving monitoring data collected from at least one monitoring site in a selected area, the monitoring data collected over a predetermined period of time, wherein the monitoring data comprises air pollution data and weather data for a section of the selected area;

mapping a grid onto a representation of the selected area;

wherein at least one cell in the grid represents the section of the selected area encompassing the at least one monitoring site;

wherein at least one cell in the grid is a gap cell that does not encompass the at least one monitoring site;

assigning an air pollution value and a weather value from the monitoring data to each cell in the grid;

generating a re-sized grid by re-sizing cells in the grid to minimize an influence attributed to atmospheric turbulence on an air pollution value assigned to each of the cells;

for each cell in the re-sized grid, eliminating an approximation of a weather influence from the air pollution value assigned to a selected cell by obtaining the selected cell's monitoring data for a time $T+\Delta T$ and a previous time $T$ and obtaining the monitoring data for the cells adjacent to the selected cell for a time $T+\Delta T$ and a previous time $T$;

using a machine learning technique to minimize an influence of wind speed and humidity in the selected cell in which the approximation of the weather influence has been eliminated, the machine learning technique using datasets trained in locations where an expected net emissions level is substantially zero, and outputting a deviation between a training level of air pollution and an actual air pollution level;

using a cluster method to find a source center of a region with high levels of pollutant emissions to approximate an influence attributed to diffusion; and providing results showing the location source of the pollutant emissions.

21. The computer program product of claim 20, further comprising minimizing the weather influence from cells adjacent to the selected cell using fluid dynamics calculations, resulting in a re-calculated air pollution value for the selected cell wherein the computer-executable instructions further comprise converting the re-calculated air pollution value for the cell to an air pollution level within a range of documented air pollution levels, to transform the air pollution value to a discrete variable which can be classified by machine learning.

* * * * *